(12) United States Patent
Ruberti et al.

(10) Patent No.: US 9,187,329 B2
(45) Date of Patent: Nov. 17, 2015

(54) MICROPARTICLE ORGANIZATION

(75) Inventors: Jeffrey W. Ruberti, Lexington, MA (US); Nima Saeidi, Allston, MA (US)

(73) Assignee: Northeastern University, Boston, MA (US)

( * ) Notice: Subject to any disclaimer, the term of this patent is extended or adjusted under 35 U.S.C. 154(b) by 812 days.

(21) Appl. No.: 13/265,729

(22) PCT Filed: Apr. 21, 2010

(86) PCT No.: PCT/US2010/031922
§ 371 (c)(1),
(2), (4) Date: Jun. 4, 2012

(87) PCT Pub. No.: WO2010/124010
PCT Pub. Date: Oct. 28, 2010

(65) Prior Publication Data
US 2014/0353873 A1  Dec. 4, 2014

Related U.S. Application Data

(60) Provisional application No. 61/171,237, filed on Apr. 21, 2009.

(51) Int. Cl.
B82B 3/00 (2006.01)
C01B 31/02 (2006.01)
B82Y 30/00 (2011.01)
B82Y 40/00 (2011.01)
C07K 14/75 (2006.01)

(52) U.S. Cl.
CPC ............... *C01B 31/0253* (2013.01); *B82B 3/00* (2013.01); *B82Y 30/00* (2013.01); *B82Y 40/00* (2013.01); *C07K 14/75* (2013.01)

(58) Field of Classification Search
None
See application file for complete search history.

(56) References Cited

U.S. PATENT DOCUMENTS

| 6,183,714 | B1  |   | 2/2001 | Smalley et al. |
| 6,921,575 | B2  | * | 7/2005 | Horiuchi et al. ............... 428/367 |
| 2006/0159722 | A1 | * | 7/2006 | Braithwaite et al. ........... 424/427 |
| 2008/0038361 | A1 |   | 2/2008 | Cheon et al. |
| 2008/0097280 | A1 |   | 4/2008 | Martin et al. |
| 2008/0159985 | A1 |   | 7/2008 | Bowlin et al. |
| 2008/0220181 | A1 |   | 9/2008 | Babu et al. |

FOREIGN PATENT DOCUMENTS

| WO | WO-00/26138     | 5/2000  |
| WO | WO-02/16257     | 2/2002  |
| WO | WO-2003/084869  | 10/2003 |
| WO | WO-2009/126958  | 10/2009 |

OTHER PUBLICATIONS

Ceballos, Experimental Neurology, 1999, Academic Press, vol. 158, pp. 290-300.*
Guo Cheng, Biomaterials, 2007, Science Direct, vol. 28, No. 6, pp. 1105-1114.*

(Continued)

*Primary Examiner* — Matthew Daniels
*Assistant Examiner* — Geralda Severe
(74) *Attorney, Agent, or Firm* — Wilmer Cutler Pickering Hale and Dorr LLP

(57) ABSTRACT

Methods and compositions are described for organizing nanoparticles or microparticles into nanostructures or microstructures using collagen as a template.

20 Claims, 6 Drawing Sheets

(56) References Cited

OTHER PUBLICATIONS

Harrison, Biomaterials, 2007, Science Direct, vol. 28, No. 2, pp. 344-353.*

Cheng Xingguo, Biomaterials, 2008, Science Direct, vol. 29, No. 22, pp. 3278-3288.*

Giraud-Guille, Comptes Rendus Chimie, 2008, Science Direct, vol. 11, pp. 245-252.*

Saeidi, Doctor of Philosophy dissertation, 2009, Northeastern University, pp. 172.*

Bailey, A.J. and Rhodes, D.N., "Irradiation-Induced Crosslinking of Collagen," *Radiat. Res.*, vol. 22, pp. 606-621 (Aug. 1964).

Cassell, et al. "Large Scale CVD Synthesis of Single-Walled Carbon Nanotubes," *J. Phys. Chem. B*, vol. 103, pp. 6484-6492 (1999).

Dai, et al., "Controlled Chemical Routes to Nanotube Architectures, Physics and Devices," *J. Phys. Chem.*, vol. 103, pp. 11246-11255 (1999).

Housley, et al., "Collagen Crosslinking: Isolation of Hydroxyaldol-Histidine, A naturally-Occurring Crosslink," *Biochem Biophys. Res. Commun.*, vol. 67, No. 2, pp. 824-830 (1975).

International Search Report and Written Opinion of the U.S. Patent and Trademark Office as International Searching Authority for International Application No. PCT/US2010/31922 mailed Jun. 29, 2010 (8 pgs.).

Journet, et al., "Large-scale Production of Single-Walled Carbon Nanotubes by the Electric-arc Technique," *Nature*, vol. 388, No. 6644, pp. 756-758 (Aug. 21, 1997).

Kong, et al., "Chemical vapor deposition of methane for single-walled carbon nanotubes," *Chem. Phys. Lett.*, vol. 292, pp. 567-574 (Aug. 14,1998).

Kong, et al., "Synthesis of Individual Single-Walled Carbon Nanotubes on Patterned Silicon Wafers," *Nature*, vol. 395, pp. 878-881 (Oct. 29, 1998).

Li, et al., "Preparation of Monodispersed Fe-Mo Nanoparticles as the Catalyst for CVD Synthesis of Carbon Nanotubes," *Chem. Mater.*, vol. 13, pp. 1008-1014 (2001).

Mechanic, G. And Tanzer, M.L., "Biochemistry of collagen crosslinking. Isolation of a new crosslink, hydroxylysinohydroxynorleucine, and its reduced precursor, dihydroxynorleucine, from bovine tendon," *Biochem Biophys. Res. Commun*, vol. 41, No. 6, pp. 1597-1604 (1970).

Mechanic, et al., "The Nature of Crosslinking in Collagens From Mineralized Tissues," *Biochem Biophys. Res. Commun.*, vol. 45, No. 3, pp. 644-653 (1971).

Nikolaev, et al., "Gas-Phase Catalytic Growth of Single-Walled Carbon Nanotubes from Carbon Monoxide," *Chem. Phys. Lett.* 313, pp. 91-97 (1999).

Ruberti, et al., "Strain-Controlled Enzymatic Cleavage of Collagen in Loaded Matrix," *Biochem. Biophys. Res. Commun.* vol. 336, pp. 483-489 (2005).

Shoshan, et al., "Studies on Collegan Crosslinking in Vivo," *Biochim Biophys. Acta*, vol. 154, No. 1, pp. 261-263 (1968).

Siegel, R.C., "Biosynthesis of Collagen Crosslinks: Increased Activity of Purified Lysyl Oxidase with Reconstituted Collagen Fibrils," *Proc. Natl. Acad. Sci. U.S.A.*, vol. 71, No. 12, pp. 4826-4830 (Dec. 1974).

Thess, et al., "Crystalline Ropes of Metallic Carbon Nanotubes," *Science*, New Series, vol. 273, No. 5274, pp. 483-487 (Jul. 26, 1996).

Zheng, et al., "Structure-Based Carbon Nanotube Sorting by Sequence-Dependent DNA Assembly," *Science*, vol. 302, pp. 1545-1548 (2003).

\* cited by examiner

MICROPARTICLE ORGANIZATION

CROSS-REFERENCE TO RELATED APPLICATIONS

This application claims the benefit of U.S. Provisional Application No. 61/171,237, filed Apr. 21, 2009, the contents of which are hereby incorporated in their entirety herein.

FIELD OF THE INVENTION

The invention relates to microparticle organization for the preparation of organic and inorganic materials.

BACKGROUND OF THE INVENTION

Carbon nanotubes (CNTs) are hexagonal networks of carbon atoms forming seamless tubes, and each end can be capped with half of a fullerene molecule. They were first reported in 1991 by Sumio Iijima who produced multi-layer concentric tubes or multi-walled CNTs by evaporating carbon in an arc discharge. CNTs possess certain electronic and mechanical properties, making them candidates for applications relating to composite materials, nanoelectronics, sensors, and electron field emitters. CNTs can be utilized individually or as an ensemble to build a variety of devices. For instance, individual nanotubes have been used as tips for scanning probe microscopy and as mechanical nano-tweezers. Ensembles of nanotubes have been used for field emission based flat-panel displays, and bulk quantities of nanotubes may be used as a high-capacity hydrogen storage media. The electronic behavior of CNTs is closely related to their structure, i.e., tip curvature, radius and composition, nanotube length, and chirality. Thus, there is a need for methods of arranging CNT structural elements, such as for electronic applications, including the development of field emission devices (FEDs). However, there is no existing method capable of organizing nanotubes, especially over large scales.

SUMMARY OF THE DISCLOSURE

The disclosure is based, at least in part, on the discovery that collagen can be used to organize carbon nanotubes. Accordingly, in one aspect, the invention features a method of organizing nanoparticles into a nanostructure, comprising: contacting a collagen template with a solution comprising (i) collagen monomers in liquid crystalline phase and (ii) nanoparticles; and assembling the collagen monomers into an ordered collagen structure by neutralizing the solution in contact with the collagen template, the ordered collagen structure directing the organization of the nanoparticles into a nanostructure. In some embodiments, the solution is a still solution.

In some embodiments, the nanoparticle has a diameter of about 1 nm to about 1 μm, about 10 nm to about 500 nm, about 20 nm to about 250 nm, about 30 nm to about 200 nm, about 1 nm to about 10 nm, about 10 nm to about 20 nm, about 20 nm to about 30 nm, about 30 nm to about 40 nm, or about 40 nm to about 50 nm. In other embodiments, the nanoparticle has an aspect ratio of at least about 2, at least about 3, at least about 4, at least about 5, at least about 6, at least about 7, at least about 8, at least about 9, at least about 10, or more.

In some embodiments, the method further comprises contacting the nanoparticles with a crosslinking agent. In some embodiments, the crosslinking agent is formaldehyde, hexamethylene diisocyanate, glutaraldehyde, a polyepoxy compound, gamma irradiation, ultraviolet irradiation with riboflavin, transglutaminase, acyl azidesglycidyl ethers, diisocyanates, hexamethylenediisocyanate, bis-epoxide, carbodiimide, dimethylsuberimidate, nordihydroguaiaretic acid, lysyl oxidase, or a combination thereof.

In other embodiments, the method further comprises removing the ordered collagen structure from the nanostructure. In certain embodiments, removing the organized collagen structure comprises contacting the ordered collagen structure with collagenase.

In some embodiments, the nanostructure is a single-walled carbon nanotube. In other embodiments, the nanostructure is a multi-walled carbon nanotube.

In some embodiments, the still solution comprises about 1% to about 99% collagen monomers. In other embodiments, the still solution comprises about 1% to about 99% nanoparticles. In yet other embodiments, the solution comprises a ratio of collagen monomers to nanoparticles of about 1% to about 99%.

In some embodiments, the collagen monomers comprise a nematic phase. In other embodiments, the collagen monomers comprise a smectic phase. In yet other embodiments, the collagen monomers comprise a cholesteric phase.

In certain embodiments, the solution comprises about 30 mg/ml to about 1000 mg/ml collagen monomers, about 30 mg/ml to about 500 mg/ml, about 40 mg/ml to about 400 mg/ml, about 50 mg/ml to about 300 mg/ml, about 60 mg/ml to about 200 mg/ml, about 70 mg/ml to about 150 mg/ml, about 80 mg/ml to about 125 mg/ml, about 90 mg/ml to about 120 mg/ml, or about 100 mg/ml collagen monomers.

In some embodiments, the method includes neutralizing the solution by adjusting the solution to a pH of about 5 to about 10, about 5.5 to about 9.5, about 6 to about 9, about 6.5 to about 8.5, or about 6.5 to about 8.

In other embodiments, the method includes neutralizing the solution in contact with the template at about 10° C. to about 39° C., at about 10° C. to about 35° C., about 15° C. to about 30° C., or about 20° C. to about 25° C.

In certain embodiments, the method further comprises applying an electric charge to the collagen template.

In particular embodiments, the collagen template comprises one or more guidance structures. In specific embodiments, the one or more guidance structures are one or more internal guidance structures and the collagen template is placed in a stationary position within the solution. In some embodiments, the guidance structures comprise a surface having a pattern of hydrophobic and hydrophilic stripes.

In other embodiments, the one or more internal guidance structures comprise a high aspect ratio geometry. In particular embodiments, the one or more internal guidance structures comprise a minor length scale of between about 14 nm and about 20 μm, for example, between about 20 nm and about 15 μm, between about 25 nm and about 10 μm, between about 30 nm and about 5 μm, between about 40 nm and about 100 nm, between about 50 nm and about 90 nm, between about 60 nm and about 80 nm, or about 70 nm.

In some embodiments, one or more of the internal guidance structures comprise a biodegradable material. In certain embodiments, the biodegradable material is silk, PLGA, or a PLA-type material (such as PDLA, PLLA, or PDLLA).

In yet other embodiments, the collagen template comprises a plurality of external guidance structures. In some embodiments, the external guidance structures have an interstructure distance of about 2 μm to about 200 μm, for example about 4 μm to about 175 μm, about 8 μm to about 150 μm, about 10 μm to about 125 μm, about 20 μm to about 100 μm, about 30 μm to about 90 μm, about 40 μm to about 80 μm, or about 50 μm to about 70 μm. In some embodiments, the collagen template comprises one or more internal guidance structures and one or more external guidance structures.

In certain embodiments, the collagen template comprises a cylindrical tube, two concentric cylindrical tubes, or two concentric hemispheres. In some embodiments, the collagen template comprises a cylindrical tube having an inner diameter of about 100 μm to about 1 mm, for example about 125 μm to about 900 μm, about 150 μm to about 800 μm, about 175 μm to about 700 μm, about 200 μm to about 600 μm, about 300 μm to about 500 μm, or about 400 μm to about 450 μm. In other embodiments, the collagen template comprises two concentric cylinders with a gap width of about 2 μm to about 4 mm, for example, about 4 μm to about 2 mm, about 8 μm to about 1 mm, about 10 μm to about 900 μm, about 20 μm to about 800 μm, about 30 μm to about 700 μm, about 40 μm to about 600 μm, about 50 μm to about 500 μm, about 100 μm to about 400 μm, or about 200 μm to about 300 μm. In yet other embodiments, the collagen template comprises two concentric hemispheres with a gap width of about 2 μm to about 4 mm, for example, about 4 μm to about 2 mm, about 8 μm to about 1 mm, about 10 μm to about 900 μm, about 20 μm to about 800 μm, about 30 μm to about 700 μm, about 40 μm to about 600 μm, about 50 μm to about 500 μm, about 100 μm to about 400 μm, or about 200 μm to about 300 μm.

In some embodiments, the collagen template comprises a scaffold that mimics a cornea, a ligament, a tendon, a meniscus, an intervertebral disk, or articular cartilage.

In certain embodiments, the collagen monomers are selected from the group consisting of Type I collagen monomers, Type II collagen monomers, Type III collagen monomers, Type V collagen monomers, Type XI collagen monomers, an MMP-resistant mutant thereof, and combinations thereof. In other embodiments, the collagen monomers are selected from the group consisting of atelo-collagen monomers, tropocollagen monomers, procollagen monomers, and combinations thereof.

In particular embodiments, the solution comprises a buffer or salt selected from the group of $CaCl_2$, NaOH, NaCl, $Na_2HPO_4$, $NaHCO_3$, Hepes, PBS, Trizma base, Tris-HCl, cell culture media, and combinations thereof.

In yet other embodiments, the solution comprises one or more co-nonsolvency agents. In certain embodiments, the co-nonsolvency agent is polyethylene glycol, hyaluronic acid, a glycosaminoglycan, a proteoglycan, or a combination thereof. In some embodiments, the glycosaminoglycan is chondroitin sulfate, hyaluronic acid, heparin, heparin sulfate, keratin sulfate, or dermatan sulfate.

In other embodiments, the solution further comprises a collagen binding agent. In some embodiments, the collagen binding agent is a proteoglycan, a glycoprotein, a collagen-binding portion thereof, or a combination thereof. In certain embodiments, the proteoglycan is lumican, decorin, biglycan, perlecan, versican, fibromodulin, aggrecan, sydecan or a combination thereof. In other embodiments, the glycoprotein is fibronectin, laminin, osteonectin, or a combination thereof.

In yet other embodiments, the ordered collagen structure is about 100 μm to about 30 cm in length, for example, about 200 μm to about 20 cm, about 400 μm to about 10 cm, about 500 μm to about 5 cm, about 750 μm to about 1 cm, about 1 mm to about 500 mm, about 10 mm to about 400 mm, about 50 mm to about 300 mm, about 100 mm to about 200 mm, or about 100 mm to about 150 mm.

In certain embodiments, the method further comprises contacting the collagen monomers in the ordered collagen structure with a crosslinking agent. In some embodiments, the crosslinking agent is formaldehyde, hexamethylene diisocyanate, glutaraldehyde, a polyepoxy compound, gamma irradiation, ultraviolet irradiation with riboflavin, transglutaminase, acyl azidesglycidyl ethers, diisocyanates, hexamethylenediisocyanate, bis-epoxide, carbodiimide, dimethylsuberimidate, nordihydroguaiaretic acid, lysyl oxidase, or a combination thereof.

In other embodiments, the method further comprises modulating the surface energy of the guidance structures. In some embodiments, the surface energy is modulated by plasma cleaning, silanization, or hydrophobic/hydrophilic bonding.

In other embodiments, the nanoparticle is a nanoparticle described herein.

The following figures are presented for the purpose of illustration only, and are not intended to be limiting.

Figure 1A:
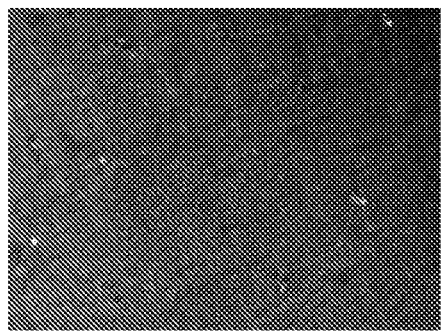
FIG. 1A is a representation of a crossed polarized microscopy image of collagen nanotube constructs showing the relatively aligned arrays.

Other features and advantages of the invention will be apparent from the following detailed description, and from the claims.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs.

DEFINITIONS

As used herein, a "collagen template" is a three-dimensional structure or substrate that controls collagen fibril organization to produce an ordered collagen structure. A collagen template creates a zone of local influence within a solution of collagen. A collagen template comprises one or a plurality of guidance structures. An ordered collagen structure can be used to organize nanoparticles or microparticles as described herein.

As used herein, a "guidance structure" is a structure with a high aspect ratio with a minor length scale of between about 14 nm and about 20 μm. The guidance structure is defined by the operative length scale of a collagen monomer.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "interstructure distance" means the distance between the outer surfaces of two adjacent guidance structures.

As used herein, "alignment" in reference to collagen fibrils means that most of the fibrils in the same radial plane in a tube wall run roughly parallel to each other. It is not meant that every fibril must be parallel to every other fibril in the plane, but that a general alignment pattern must be discernable.

As used herein, a "fibril" is an association of several collagen monomers into a structure that appears fibrous with suitable magnification.

As used herein, "collagen" means a protein component of an extracellular matrix having a tertiary structure that includes polypeptide chains intertwining to form a collagen triple helix or having a characteristic amino acid composition comprising Gly-X-Y repeat units, or a fragment thereof. Collagens can be any collagen known in the art (e.g., one of collagen Type 1-29).

As used herein, "nanoparticle" means any particle having a minor diameter of about 1 nm to about 1,000 nm and having an aspect ratio of at least about 2.

As used herein, "microparticle" means any particle having a minor diameter of about 1 μm to about 1,000 μm and having an aspect ratio of at least about 2.

As used herein, "carbon nanotube" refers to a hollow cylindrical article composed primarily of carbon atoms. A carbon nanotube can have a diameter of about 1 nm to about 1 μm and a ratio of length to diameter (i.e., aspect ratio) of at least about 2.

GENERAL

The methods described herein are based, at least in part, on the discovery that microparticles or nanoparticles, such as carbon nanotubes, can be organized into microstructures or nanostructures using collagen as a template. Producing aligned, single-walled carbon nanotubes (swCNTs) has numerous potential applications from the generation of transistors and electrical switches to the production of exceedingly strong materials. This disclosure uses the ability of collagen monomers to form organized aligned structures when highly concentrated (as described in, e.g., PCT/US09/40364) to provide a guidance nanotube template for co-dispersed carbon nanotubes. This approach is feasible because single-walled carbon nanotubes are geometrically similar to collagen monomers (300 nm×1.5 nm). This disclosure includes the ability to produce organized swCNTs by dispersing the swCNTs (1%-75% molar fraction relative to collagen) in a dense solution of collagen monomers (30 mg/ml-500 mg/ml). Collagen, which behaves as a liquid crystal, strongly influences the organization of the swCNTs because they are geometrically similar. Following the production of organization in the mixed solution of collagen and swCNTs, the collagen can be removed by a number of methods. The organization of the swCNTs during collagen removal can be preserved, such as by crosslinking functional groups or by maintaining a high osmotic pressurization to confine the swCNTs. Collagen can be removed in a number of ways, such as enzymatically by exposure to collagenase (bacterial, MMP and others), or by heat denaturation followed by exposure to gelatinase leaving behind the organized swCNTs provided they are sufficiently stabilized.

Microparticles and Nanoparticles

The methods described herein can be used to organize microparticles and nanoparticles into microstructures or nanostructures. In some embodiments, the nanostructures are carbon nanotubes. Carbon nanotubes are carbon nanostructures in the form of tubes, ranging in general in diameter from about 0.5-200 nm, (more typically for single-walled carbon nanotubes from about 0.5-5 nm). The aspect ratio of nanotube length to nanotube diameter is greater than about 5, ranges from 10-2000 and more typically 10-100. Carbon nanotubes may be single-walled nanotubes (a single tube) or multi-walled comprising with one or more smaller diameter tubes within larger diameter tubes. Carbon nanotubes are available from various sources, including commercial sources (e.g., Helix Materials Solutions, Richardson, Tex.), or synthesis employing, among others, arc discharge, laser vaporization, the high pressure carbon monoxide processes.

Exemplary methods for synthesis of carbon nanotubes are described in, e.g., U.S. Pat. No. 6,183,714; WO 00/26138; WO 03/084869; WO 02/16257; Thess et al., *Science* 273:483 (1996); Journet et al., *Nature* 388, 756 (1997); Nikolaev et al., *Chem. Phys. Lett.* 313:91 (1999); Kong et al., *Chem. Phys. Lett.* 292: 567 (1998); Kong et al., *Nature* 395:878 (1998); Cassell et al., *J. Phys. Chem.* 103:6484 (1999); Dai et al., *J. Phys. Chem.* 103:11246 (1999); and Li et al., *Chem. Mater.* 13:1008 (2001).

A method for separating single-walled carbon nanotubes by diameter and conformation based on electronic and optical properties has been reported (WO 03/084869). The method can be used to prepare carbon nanotube preparations having enhanced amounts of certain single walled carbon nanotube types (see, e.g., Zheng et al., *Science* 302:1545 (2003)).

Other microparticles and nanoparticles include organic or inorganic materials. In particular instances, the microparticles or nanoparticles are ceramics, metals, or composites. Nonlimiting examples are metallic (e.g., Ni, Pt, Au), semiconducting (e.g., Si, InP, GaN), and insulating (e.g., $SiO_2$, $TiO_2$) materials.

Collagen

The methods described herein involve using collagen to produce organized microstructures or nanostructures. Collagen is the most abundant protein in the extracellular matrix (ECM) of vertebrates and is the most common structural molecule in tensile load-bearing applications.

More than 29 different collagenous sequences are known. Fibrillar collagens (e.g., Types I, II, III, V and XI) are the principal structural component in load-bearing extracellular matrix (ECM), which provides a network for cells to interact and form three dimensional, multi-cellular organisms. Collagen possesses a linear-helical structure comprising three left-handed helical alpha chains whose complementary amino acid sequence results in the formation of a right-handed supramolecular triple helix. Collagen contains the repetitive sequence amino acid sequence Gly-X-Y, where X and Y are usually proline and hydroxyproline, respectively.

As described herein, collagen is not a passively manipulated element, but rather a principal component in a cooperative engineering material system, a system that significantly enhances the ability of fibroblastic cells to produce and optimize load-bearing tissue.

Any known collagen can be used in the methods described herein and can be isolated or derived from a natural source, manufactured biochemically or synthetically, produced through genetic engineering, or produced through any other means or combinations thereof. In addition, collagen is commercially available (e.g., from Inamed Biomaterials, Fremont, Calif.; and FibroGen, Inc., San Francisco, Calif.). Natural sources include, but are not limited to, collagens produced by or contained within the tissue of living organisms (e.g., cows, pigs, birds, fish, rabbits, sheep, mice, rats, and humans). Further, natural collagen can be obtained from, for example, tendons, bones, cartilage, skin, or any other organ by any known extraction method. Exemplary sources include rat tail tendon and calf skin.

Some collagens that are useful in the methods described herein include, but are not limited to, collagen Types I, II, III, IV, V, VI, VII, VIII, IX, X, XI, XII, XIII, XIV, XV, XVI, XVII, XVIII, and XIX. Synthetic collagen can include collagen produced by any artificial means, and numerous methods for producing collagens and other proteins known in the art can be used. For example, synthetic collagen can be prepared using specific sequences, such as specific amino acids that are the same or that differ from natural collagen. Engineered collagen can be produced by any method known in the art including, for example, polypeptide synthesis.

Other Molecules

In addition to collagen, other molecules can be used to organize microparticles or nanoparticles into microstructures or nanostructures in the methods described herein. Such molecules include molecules with self-organizing and/or liquid crystalline properties. Specific, nonlimiting examples include actin and microtubules.

Methods of Organizing Microstructures and Nanostructures

Concentrating and Precipitating Collagen

In some instances, the methods described herein include confining a solution of collagen monomers within a collagen template having a defined confinement geometry (e.g., having defined external guidance structures). The solution can include any type of collagen monomers.

The collagen in solution can be in a liquid crystalline phase, e.g., in nematic, smectic, or cholesteric phase. In certain instances, the concentration of collagen monomers in the solution is between about 30 mg/ml and about 500 mg/ml. In other instances, the collagen solution includes a buffer. Examples of buffers include, without limitation, $CaCl_2$, NaOH, NaCl, $Na_2HPO_4$, $NaHCO_3$, Hepes, PBS, Tris, cell culture media, and combinations thereof.

By confining the solution of collagen monomers within external guidance structures, the collagen monomers are induced to precipitate and to form collagen arrays having a desired architecture. In one exemplary method, collagen monomers are concentrated to about 100 mg/ml and are confined between featureless planar glass coverslips separated by about 40μ, leading to fibril precipitation from the solution with a high-degree of alignment in planes parallel to the coverslips. In this situation, the coverslips provide external guidance structures that induce the alignment of the fibrils. Further, the collagen fibrils can form layers in which the orientation of the alignment of the fibrils can change direction, forming a natural load-bearing structure similar to native collagen organization found in cornea, bone, blood vessel intima or adventitia, and annulus fibrosus. Thus, the concentration and confinement of collagen in axially symmetric geometries can result in the formation of structures similar to any collagenous tissue, such as ligament or tendon.

In other methods, the local organization of collagen is controlled by using internal collagen templates (e.g., internal guidance structures). While not wishing to be bound by theory, it is believed that such internal collagen templates mimic embedded fibroblasts (or fibroblast filipodia) to influence the local organization of collagen fibrils. In certain instances, the internal collagen template is made of a biodegradable polymer. Nonlimiting examples of biodegradable polymers include silk, poly(lactide), poly(glycolic acid), poly(lactide-co-glycolide), poly(caprolactone), polycarbonates, polyamides, polyanhydrides, polyamino acids, polyortho esters, polyacetals, polycyanoacrylates, and degradable polyurethanes.

In one exemplary method, an internal collagen template is made of fine degradable filaments that are woven into a sparse scaffold. The scaffold can then be immersed in a solution of concentrated collagen monomers, which induces the alignment of the precipitating collagen to follow the internal collagen template. The spacing and size of the internal collagen template (e.g., biodegradable filaments) can be arranged to result in a particular collagen fibrillar organization of interest. Thus, the use of internal guidance structures allows internal control over the organization of collagen, such as solutions of collagen monomers confined within a particular geometry (e.g., within external guidance structures).

Organizing Microstructures and Nanostructures

As described herein, the concentrated and precipitated collagen is organized into ordered collagen structures, which organize microstructures and nanostructures, such as carbon nanotubes. By codispersing microstructures or nanostructures with a solution of collagen monomers followed by inducing the alignment of collagen monomers into collagen fibrils, the collagen fibrils form an organized collagen structure that directs the organization of the microstructure or nanostructure, such as a carbon nanotube. The ratio of collagen monomers and microstructures or nanostructures in solution can vary. In particular examples, the ratio of collagen monomers to microstructures or nanostructures is about 1% to about 99%.

Modifying External and Internal Templates

The external and internal collagen templates (e.g., external and internal guidance structures) can be modified to influence the collagen fibrillar organization. For example, using known methods, the surfaces of the external and internal collagen templates can be plasma cleaned, patterned, or functionalized in other ways to control the local organization of the interfacing fibrils to produce collagen arrays. In particular methods, the surfaces of the external and/or internal collagen templates are silanated or carbodiimidated using known methods.

In some instances, the surface charges of collagen molecules can be used to direct the process of collagen assembly by applying an electric charge to one or more surfaces of the external and/or internal collagen templates. In particular methods, collagen molecules can be confined between two metallic plates containing an electrical field to direct the assembly of collagen. In other situations, the amount of free ion charges in the solution can be altered to change the degree of variation in alignment between layers.

Auxiliary Molecules

The methods described herein can include the use of one or more auxiliary molecules, e.g., collagen modulating molecules such as extracellular matrix molecules. Such molecules include, but are not limited to, proteoglycans (such as perlecan, versican, syndecan, decorin, lumican, and biglycan), proteoglycan core proteins, glycosaminoglycans (such as hyaluronic acid, chondroitin-4 sulfate, chondroitin-6 sulfate, dermatan sulfate, heparin, heparin sulfate, and keratan sulfate), Type V collagen, fibronectin, or any molecule that competes with collagen for available water (such as polyethylene glycol). Such molecules can be added to a solution containing collagen monomers prior to or following the precipitation of collagen as described herein.

These auxiliary molecules can be used to increase the rate of the process and higher order organization. The ratio of auxiliary molecule to collagen can depend on the type of the molecules, and can range from about 10% to about 50%.

Methods of Strain Stabilization, Monomer Incorporation and Enzymatic Degradation of Collagen Some of the methods described herein are based, at least in part, on the discovery of a strain-dependent mechanism that can modulate collagen fibril susceptibility to enzymatic degradation. This mechanism can produce a physicochemical change at the matrix level that is bound to fibril strain. Based on this "strain-stabilization of collagen" mechanism, tensile strains can provide a robust signal, leading to a load-controlled differential degradation (catabolism) of collagen in extracellular matrix. Further, tensile strains on collagen fibrils can provide a signal, leading to the incorporation of collagen monomers into loaded fibrils (this is monomer incorporation). In some instances, the adaptive remodelling response of load-bearing ECM can be controlled by collagen and its complement enzymes (e.g., bacterial collagenase, MMPs, and cathepsins), which couple the control signal (i.e., mechanical load) to a physicochemical change in the collagen molecules or fibrils. In addition, this mechanism can relieve fibroblasts of the burden of "knowing" which fibrils to degrade during remodelling and which to reinforce. Based on this mechanism, load-stimulated fibroblasts can produce a load-adapted morphological change during, e.g., epigenetic connective tissue remodelling, repair, homeostasis and disease.

In some instances, collagen is precipitated as described herein, and the collagen organization is further refined by subjecting the initial collagenous construct to cross-linking, mechanical strain, and/or enzymes to cull unwanted (unstrained) fibrils (see, e.g., Ruberti et al., *Biochem. Biophys. Res. Commun.* 336:483-489 (2005)).

Mechanical strain can be applied to collagen fibrils using, e.g., a microchamber (see, e.g., PCT/US09/40364). In such methods, the collagen can be fixed to grips in a microchamber by, e.g., direct clamping or by adhesives (such as cyanoacrylates). In some situations, the collagen is affixed to functionalized micropipettes as described herein. During the loading of mechanical strain, auxiliary molecules can optionally be included. In addition, hydroxyapetite and noncollagenous proteins can be added to calcify the system during loading.

In some situations, prior to the loading of the construct, collagen fibrils or carbon nanotubes are cross-linked, such as to increase stability. Any suitable crosslinking agent known in the art can be used including, without limitation, formaldehyde, hexamethylene diisocyanate, glutaraldehyde, polyepoxy compounds, gamma irradiation, and ultraviolet irradiation with riboflavin. The crosslinking can be performed by any known method (see, e.g., Bailey et al., *Radiat. Res.* 22:606-621 (1964); Housley et al., *Biochem. Biophys. Res. Commun.* 67:824-830 (1975); Siegel, *Proc. Natl. Acad. Sci. U.S.A.* 71:4826-4830 (1974); Mechanic et al., *Biochem. Biophys. Res. Commun.* 45:644-653 (1971); Mechanic et al., *Biochem. Biophys. Res. Commun.* 41:1597-1604 (1970); and Shoshan et al., *Biochim. Biophys. Acta* 154:261-263 (1968)).

Enzymes

The methods described herein can include degradation of organized collagen structures after microstructure or nanostructure organization. Degradation can be performed using enzymes, such as collagen-degrading enzymes including, without limitation, collagenase (e.g., bacterial collagenase), cathepsin, and matrix metalloproteases (MMPs). Such enzymes are commercially available, e.g., from Sigma Aldrich. The enzyme can be added to the culture medium which is then introduced to the collagen or other structural material.

The invention is further illustrated by the following examples. The examples are provided for illustrative purposes only. They are not to be construed as limiting the scope or content of the invention in any way.

EXAMPLES

Example 1

In Vitro Organization of Carbon Nanotubes Using Collagen

Carbon nanotubes were mixed with collagen solution (3 mg/mL acidic solution of pepsin-extracted, atelo, type I bovine collagen monomers (PURECOL®, Inamed, Freemont, Calif.)) in the ratio of 1:1. The concentration procedure was performed by dialyzing the mixture against 40% solution of polyethylene glycol (PEG, 20 kMWCO, Sigma-Aldrich, St. Louis, Mo.) at 4° C. The dialyzing procedure proceeded until the concentration of the collagen molecules reached the range of 175±25 mg/mL. Then to reach the final concentration of 375±25 mg/mL, the dialyzing was further proceeded by injecting the solution into a dialysis cassette and dispensing the cassette in the PEG solution. The collagen solution was then neutralized (by titrating the PEG solution and letting the system to equilibrate) and transferred to a 37° C. oven. The SWNT/collagenous constructs were then carefully removed for further ultra-structural assessments using Differential interference contrast (DIC), Scanning Electron Microscopy (SEM), and standard Transmission Electron Microscopy (sTEM). At least seven experiments at each concentration range were performed.

Figure 1B:
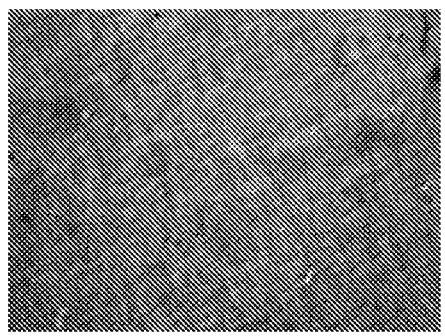
FIG. 1B is a representation of a crossed polarized microscopy image of collagen nanotube constructs showing the relatively aligned arrays.
Figure 1C:
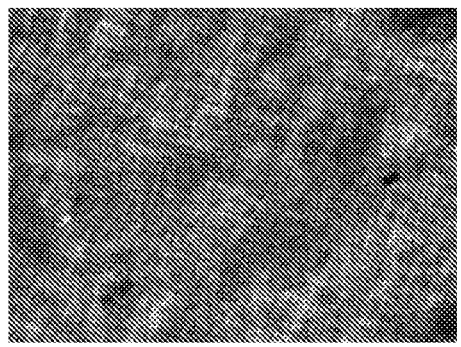
FIG. 1C is a representation of a polarized microscopy image of collagen nanotube constructs taken at the interface between two layers within a construct showing orthogonal lamellae.
Figure 2A:
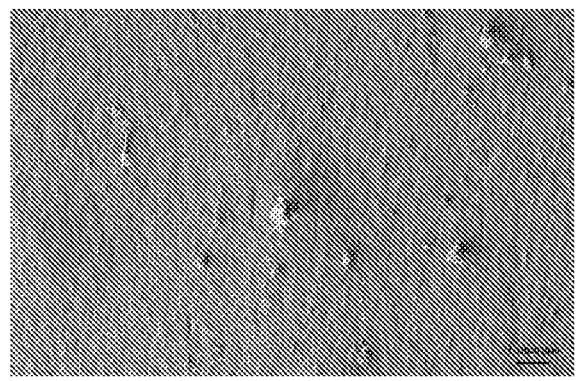
FIG. 2A is a representation of an en face scanning electron microscopy (SEM) image of collagen nanotube constructs at low magnification showing that the construct comprises aligned arrays.
Figure 2B:
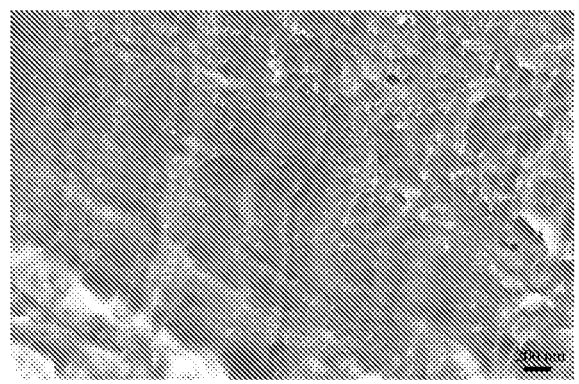
FIG. 2B is a representation of a cross sectional SEM image of collagen nanotube constructs at high magnification showing multi-layer constructs.
Figure 2C:
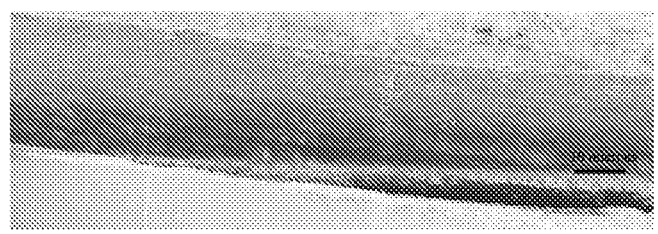
FIG. 2C is a representation of a cross sectional SEM image of collagen nanotube constructs at low magnification.
Figure 2D:
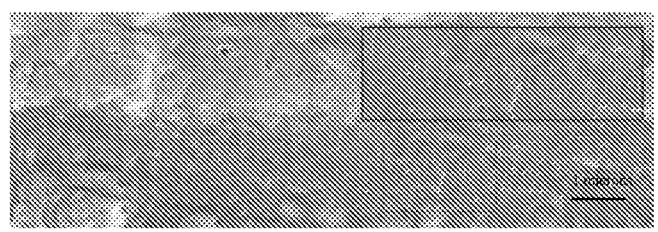
FIG. 2D is a representation of a cross sectional SEM image of collagen nanotube constructs at high magnification showing multi-layer constructs.
Figure 3:
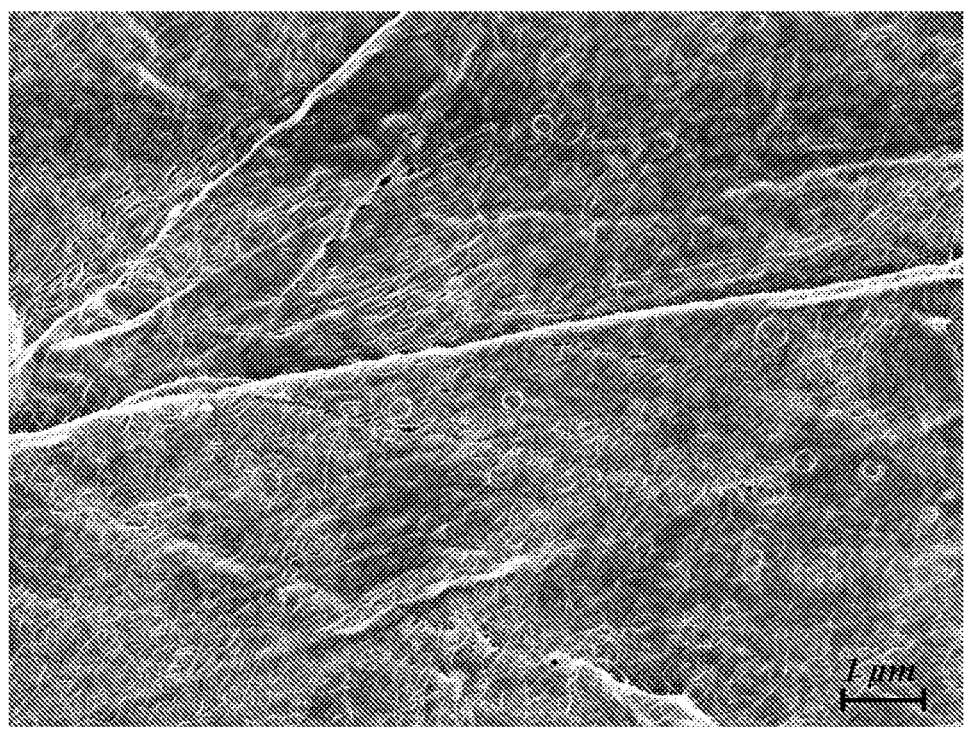
FIG. 3 is a representation of an SEM image of 100% carbon nanotubes concentrated against 40% PEG for 2 weeks. These appear conductive, but not completely organized.

As shown in FIGS. 1-3, there was very little disruptive influence of the nanotubes on the collagen organization at low loading concentrations of nanotubes into the liquid crystal collagen. At higher concentrations of nanotubes there was less organization.

Example 2

Collagen-Mediated Organization of Microstructures

The ability of collagen to organize microstructures is assessed by first processing coatings with lamellar defects and producing microparticles that can be combined with collagen for alignment into organized microparticles.

Systematic Processing and Post-Processing of Ceramic Coatings with Lamellar Defects Specific process input values are determined to fabricate lamellar structures (LS) with intended plate thickness, width and gap spacing distribution. First, ceramic powders (such as YSZ, $Al_2O_3$, or $TiO_2$) are obtained from commercial sources. Powders are fed into Air Plasma Spray (APS—high temperature, low velocity) and High Velocity Oxy Fuel (HVOF—lower temperature, high velocity) torches (Center for Thermal Spray Research, SUNY Stony Brook). Torch input parameters (current, gas flow rate) are correlated with in-flight particle state (Temperature, Velocity) to calculate 'melting index' (MI). In addition, the effects of input parameters on interfacial geometry (thickness, morphology, orientation, connectivity) within the lamellar structure are assessed. Low-strain in-plane mechanical cycling is used as a post-processing technique for further control over gap geometry, and enhanced collagen infiltration. Coatings are deposited on constant strain cantilevers, and mechanically cycled via beam bending to produce the desired strains.

For assessment, LS architecture is examined via optical microscopy and SEM in cross-section, using known image analysis methods. In particular, interface morphology (roughness) is examined locally using HRSEM. In addition, supplemental information is obtained via small angle neutron scattering (SANS).

This method provides specific design space of inorganic lamellar structures, for (i) infiltration with collagen or other organics and (ii) realizable architectures for input into multi-scale computational models. LS are designed with 'brick' particle thickness controllable within approximately 250 nm, gap spacing within approximately 10 nm, and gap length within half a 'brick' particle width. Optimum conditions for collagen infiltration and LS regularity are developed via a two stage process of (i) high velocity, high-flattening impact of particles (with small interfacial gaps) and (ii) increase in gap area via post-deposit fatigue processing.

Systematic Processing of Ceramic Particles with Designed Geometry

Figure 4:
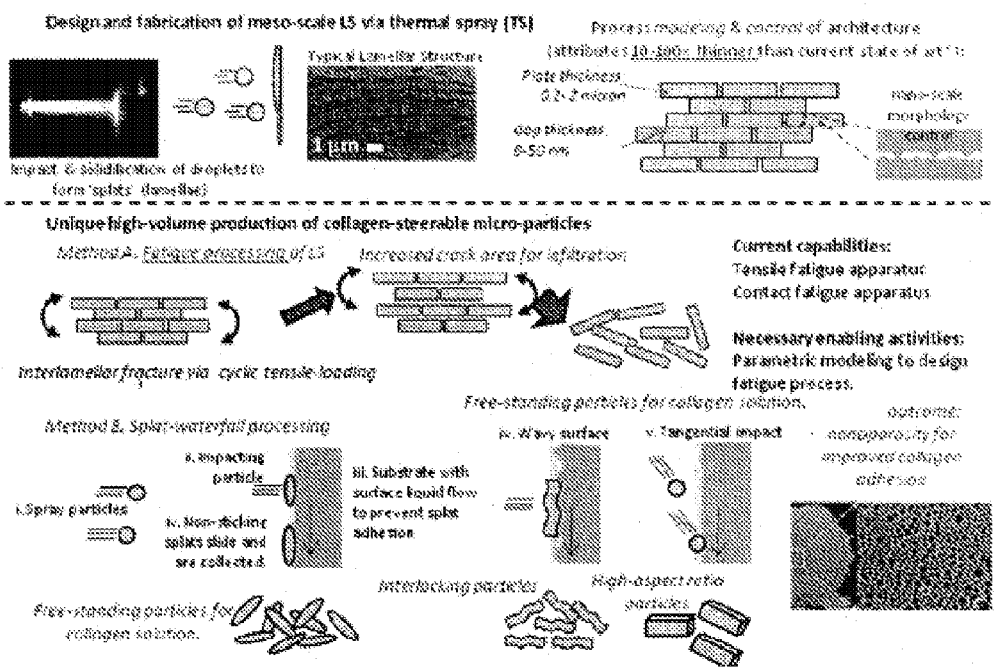
FIG. 4A is a schematic illustration of a method of designing and fabricating lamellar structures.
FIG. 4B is a schematic illustration of methods of producing collagen-steerable microparticles.

A high-volume process is established for production of impacted particles with highly controllable geometry, by recourse to TS impact processing. Powders (down to 10 micron diameter) and torch parameters are selected as described in Example 2 and are used to create and collect individual particles that are not bonded to the substrate nor each other. A novel 'waterfall processing' system is used, which is a substrate with a thin downward flow of liquid (such as water) leading to a collection unit. Molten particles impact on the substrate and flatten, but adhesion is prevented by the liquid layer and the particles are driven downward for collection. Flattening ratio is designed via process parameters and fluid impact models known in the art. In addition, substrates are prepared with varying degrees of roughness or waviness, to produce particles having interlocking capabilities. Finally, particles are impacted on substrates at non-normal orientation (as shown in FIG. 4), and in combination with 'channels', to produce higher-aspect ratio particles.

For assessment, particles are pulled out of the collection unit via 'scooping' on a substrate, and examined under optical microscopy and SEM. Distributions of properties, such as aspect ratios, are correlated with batch conditions. In addition, some process conditions lead to a 'bubbly' bottom surface of splats, due to outgassing of the liquid layer, or impact-induced depressurization. In some cases, the bubbles have sub-micron dimension, which lead to further design considerations for interaction with collagen, i.e. increased adhesion.

Organization of Microparticle "Bricks" by Collagen

Figure 5:
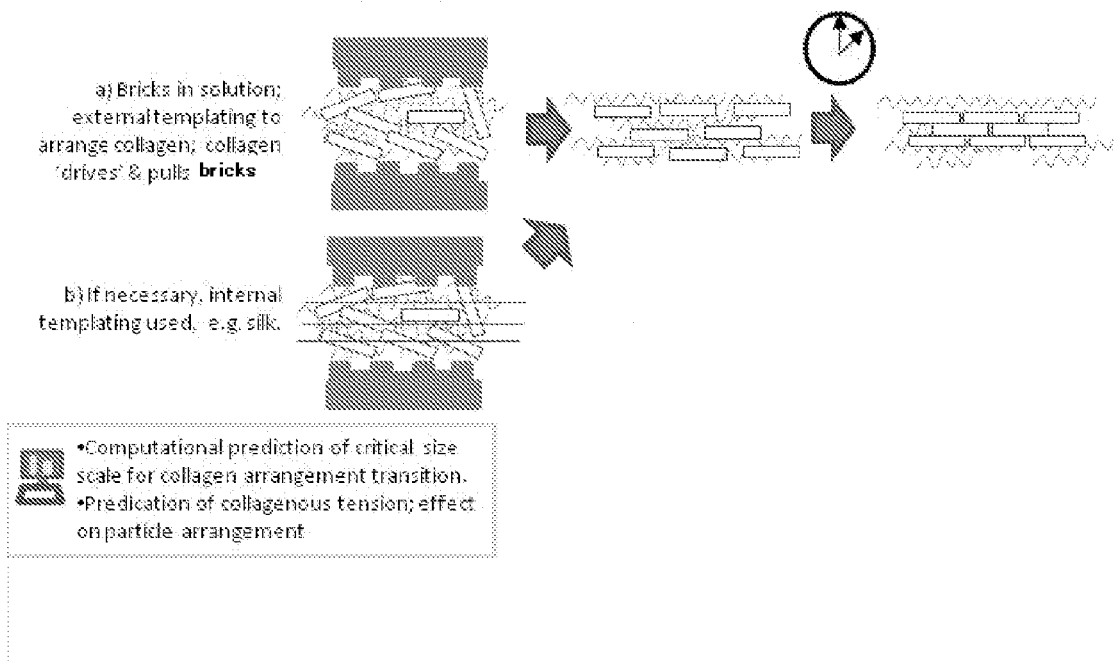
FIG. 5 is a schematic illustration of a method of particle arrangement by collagen.

As shown in FIG. 5, particles (depicted as "bricks") are combined with collagen in solution in the presence of external templates with or without internal templates. The assembly of collagen into organized collagen structures "drives" and pulls particles into organized arrangements, as depicted.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of organizing nanoparticles into a nanostructure, comprising:
   contacting a collagen template with a still solution comprising (i) collagen monomers in liquid crystalline phase and (ii) nanoparticles; and
   assembling the collagen monomers into an ordered collagen structure by neutralizing the solution in contact with the collagen template, the ordered collagen structure directing the organization of the nanoparticles into a nanostructure.

2. The method of claim 1, further comprising crosslinking functional groups on the nanoparticles to stabilize the nanostructure.

3. The method of claim 1, further comprising removing the ordered collagen structure from the nanostructure.

4. The method of claim 1, wherein the nanostructure is selected from the group consisting of a single-walled carbon nanotube and a multi-walled carbon nanotube.

5. The method of claim 1, wherein the collagen monomers comprise a phase selected from the group consisting of a nematic phase, a smectic phase, a cholesteric phase, and mixtures thereof.

6. The method of claim 1, wherein the solution comprises about 30 mg/ml to about 500 mg/ml collagen monomers.

7. The method of claim 1, wherein the neutralizing step comprises adjusting the solution to a pH of about 5 to about 10.

8. The method of claim 7, further comprising neutralizing the solution in contact with the collagen template at about 10° C. to about 39° C.

9. The method of claim 1, wherein the collagen template comprises one or more guidance structures comprising one or more internal guidance structures, and wherein the collagen template is placed in a stationary position within the solution.

10. The method of claim 9, wherein the one or more internal guidance structures comprise a high aspect ratio geometry.

11. The method of claim 10, wherein the one or more internal guidance structures comprise a minor length scale of between about 14 nm and about 20 µm.

12. The method of claim 1, wherein the collagen template comprises a plurality of external guidance structures having an interstructure distance of about 2 µm to about 200 µm.

13. The method of claim 1, wherein the collagen template comprises a cylindrical tube, two concentric cylindrical tubes, or two concentric hemispheres.

14. The method of claim 13, wherein the collagen template comprises a cylindrical tube having an inner diameter of about 100 µm to about 1 mm.

15. The method of claim 13, wherein the collagen template comprises two concentric cylinders with a gap width of about 2 μm to about 4 mm.

16. The method of claim 13, wherein the collagen template comprises two concentric hemispheres with a gap width of about 2 μm to about 4 mm.

17. The method of claim 1, wherein the collagen template comprises one or more internal guidance structures and one or more external guidance structures.

18. The method of claim 1, wherein the solution comprises one or more co-nonsolvency agents and/or a collagen binding agent.

19. The method of claim 1, further comprising applying an electric charge to the contacted collagen template.

20. The method of claim 1, wherein the ordered collagen structure is about 100 μm to about 30 cm in length.

\* \* \* \* \*